United States Patent [19]

Jamas et al.

[11] Patent Number: 4,992,540
[45] Date of Patent: * Feb. 12, 1991

[54] GLUCAN COMPOSITION AND PROCESS FOR PREPARATION THEREOF

[75] Inventors: Spiros Jamas; ChoKyun Rha; Anthony J. Sinskey, all of Boston, Mass.

[73] Assignee: Massachusetts Institute of Technology, Cambridge, Mass.

[*] Notice: The portion of the term of this patent subsequent to Mar. 7, 2006 has been disclaimed.

[21] Appl. No.: 297,982

[22] Filed: Jan. 17, 1989

Related U.S. Application Data

[63] Continuation-in-part of Ser. No. 675,927, Nov. 28, 1984, Pat. No. 4,810,646.

[51] Int. Cl.$^5$ .................... C08B 37/00; C12N 1/18; C12P 19/04
[52] U.S. Cl. ..................... 536/123; 435/101; 435/255; 435/256; 536/114; 536/121; 536/124
[58] Field of Search ............ 435/101, 255, 256; 536/114, 123, 124, 121

[56] References Cited

U.S. PATENT DOCUMENTS

| | | | |
|---|---|---|---|
| 4,075,405 | 2/1978 | Takahashi et al. | 536/114 |
| 4,707,471 | 11/1987 | Larm et al. | 536/1.1 |
| 4,769,363 | 9/1988 | Misaki et al. | 536/1.1 |
| 4,806,474 | 2/1989 | Hershberger | 536/20 |
| 4,810,646 | 3/1989 | Jamas et al. | 536/123 |
| 4,835,265 | 5/1989 | Muzzarelli | 536/18.5 |
| 4,877,777 | 10/1989 | DiLuzio | 514/54 |

OTHER PUBLICATIONS

S. Jamas et al., *Biotechnology and Bioengineering*, 28:769-784 (1986).
J. H. Sietsma et al., *Journal of General Microbiology*, 125:209-212 (1981).
J. H. Sietsma et al., *Journal of General Microbiology*, 114:99-108 (1979).
D. J. Manners, et al., *Biochemistry Journal*, 135:31-36 (1973).
D. R. Kreger, et al., *Journal of General Microbiology*, 92:207-220 (1975).
M. Kopecka, et al., *The Journal of Cell Biology*, 62:66-76 (1974).
D. J. Manners et al., *Biochemistry Journal*, 135:19-30 (1973).
W. Z. Hassid et al., *J. American Chemical Society*, 63:295-298 (1941).
N. R. DiLuzio et al., *International Journal of Cancer*, 24:773-779 (1979).

*Primary Examiner*—Ronald W. Griffin
*Attorney, Agent, or Firm*—Hamilton, Brook, Smith & Reynolds

[57] ABSTRACT

Three dimensional glucan matrix compositions are prepared by separating growing yeast from its growth medium, subjecting the yeast with cell walls intact to an alkali material, thereby extracting whole glucan particles having an intact cell wall structure. The whole glucans can then, optionally, be treated with acetic acid to alter the $\beta(1-6)$ linkages, or with glucanase to alter the $\beta(1-3)$ linkages. The glucans have viscosity characteristics dependent upon the strain of yeast utilized and are useful as stabilizers or thickeners.

25 Claims, 3 Drawing Sheets

VISCOSITY PROFILES OF YEAST GLUCAN COMPARING DIFFERENT CELL MORPHOLOGIES

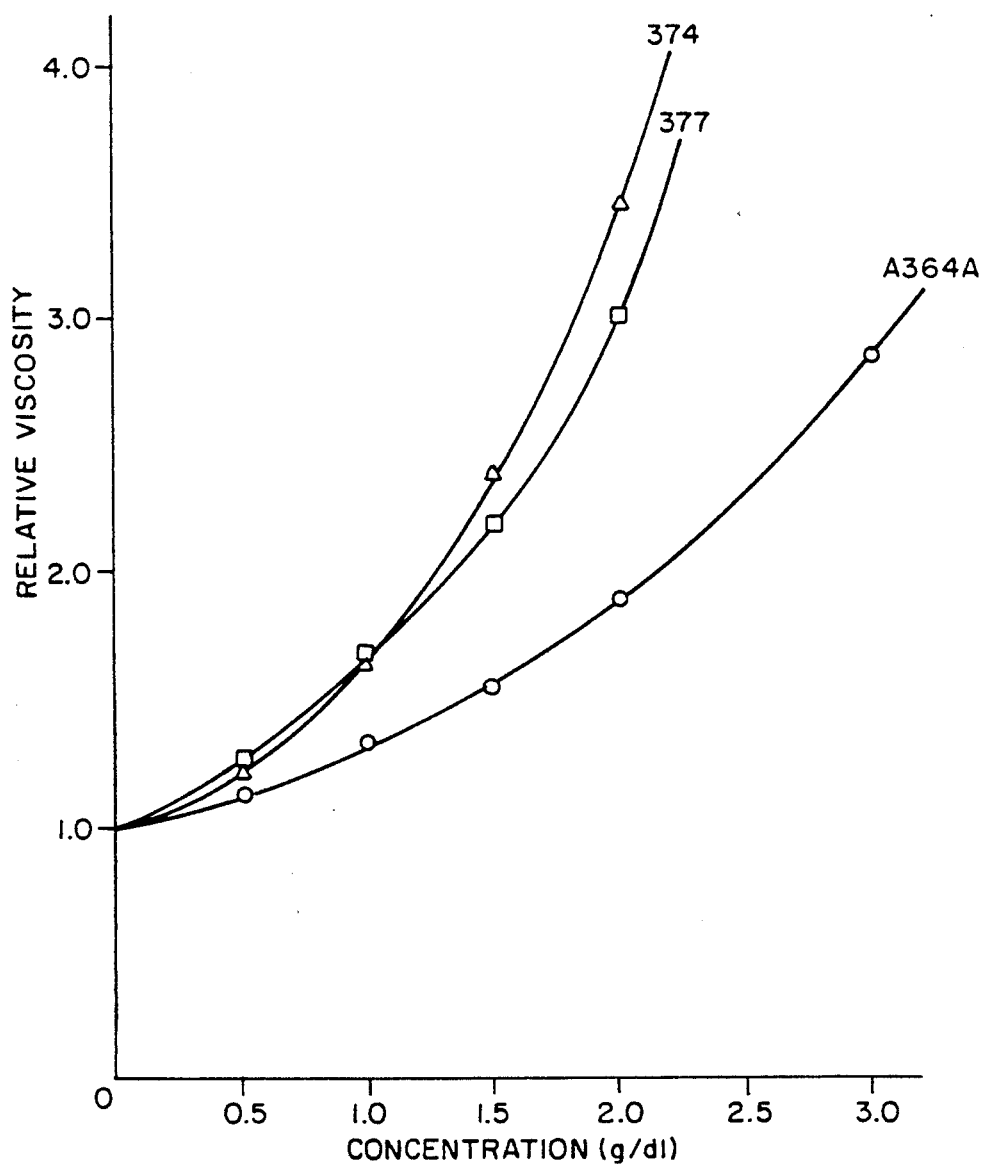
FIG. 1. VISCOSITY PROFILES OF YEAST GLUCAN COMPARING DIFFERENT CELL MORPHOLOGIES

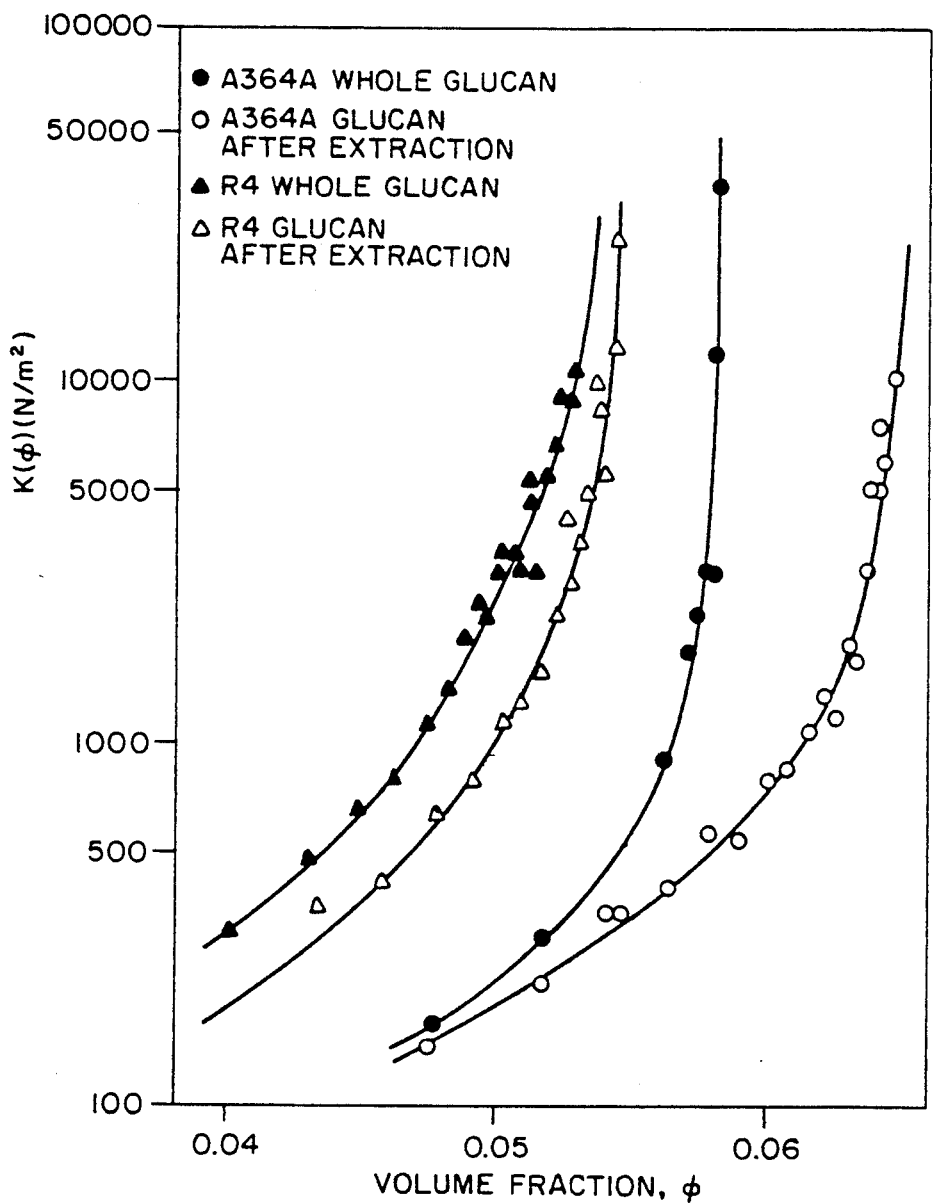
FIG. 2. PLOT OF THE NETWORK-COMPRESSION MODULUS VS. VOLUME FRACTION GLUCAN SUSPENSIONS (TIME = 60 MINUTES)

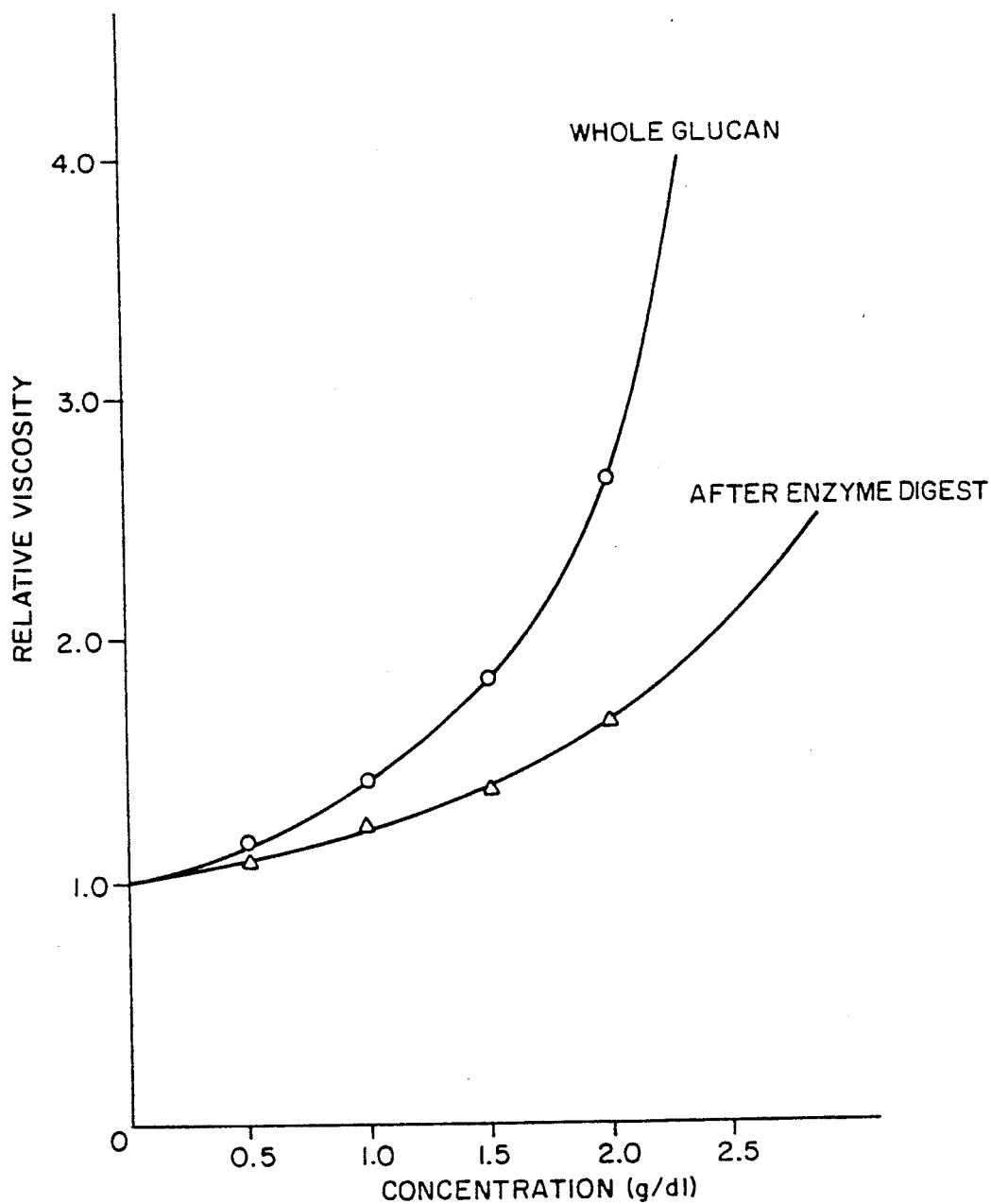
FIG. 3. VISCOSITY PROFILE OF A364A GLUCAN SHOWING THE EFFECT OF 4h LAMINARINASE DIGEST

GLUCAN COMPOSITION AND PROCESS FOR PREPARATION THEREOF

RELATED APPLICATIONS

This application is a continuation-in-part of U.S. Ser. No. 675,927, filed Nov. 28, 1984, now U.S. Pat. No. 4,810,646, entitled "Glucan Compositions And Process For Preparation Thereof" by S. Jamas, C. K. Rha and A. J. Sinskey.

FIELD OF INVENTION

The present invention relates to biopolymer engineering.

BACKGROUND OF THE INVENTION

The food industry uses many naturally derived polysaccharides as stabilizers and thickeners. Other industries use polysaccharides as water treatment chemicals, viscosifiers, thickeners and as surface active materials. Products such as carrageenan, alginate and starch, exhibit unique structural and rheological properties such as yield stress and an ability to increase the viscosity in an aqueous environment. The specific structure-function relationships of these biopolymers depend on the individual components such as monomers or repeating units and their chemical linkages.

Polysaccharides which form the bulk of biopolymers in the microbial world have already been noted for their structural importance and are responsible for maintaining the integrity of bacteria and fungi. With the advent of genetic engineering, biosynthesis and manufacture of these biopolymers can be directed to produce molecules with altered physical properties.

Yeast has historically earned its role as an important food grade and industrial organism. The cell wall of *Saccharomyces cerevisiae* is mainly composed of $\beta$-linked glucan. This polymer is responsible for the shape and mechanical strength of the cell walls. The glucan is mainly composed of a backbone chain of $\beta(1-3)$ linked glucose units with a low degree of inter and intramolecular branching through $\beta(1-6)$ linkages. A minor component that consists mainly of a highly branched $\beta(1-6)$ linked glucan is closely associated with the main component and both comprise the alkali insoluble glucan fraction.

The following articles deal with the structure of glucans: "The Structure of a $\beta$-(1-6)-D-Glucan from Yeast Cell Walls", by Manners et al., *Biochem. J.*, (1973) 135:31-36; "Evidence for Covalent Linkages between Chitin and $\beta$-Glucan in Fungal Wall", by Sietsma et al., *Journal of General Microbiology* (1979), 114:99-108; "Demonstration of a Fibrillar Component in the Cell Wall of the Yeast *Saccharomyces cervisiae* and its Chemical Nature", by Kopecka et al., *The Journal of Cell Biology*, 62 (1974), 66-76; "On the Nature and Formation of the Fibrillar Nets Produced by Photoplasts *Saccharomyces cerevisiae* in Liquid Media: An Electronmicroscopic, X-Ray Diffraction and Chemical Study", by Kreger et al., *Journal of General Microbiology*, (1975), 92:202-220; "Short Communication Solubility of (1-3)-$\beta$-D-(1-6)-$\beta$-D-glucan in Fungal Walls: Importance of Presumed Linkage between Glucan and Chitin", by Sietsma and Wessels, *Journal of General Micro-biology*, (1981), 125:209-212; "The Molecular Constitution Of An Insoluble Polysaccharide From Yeast, *Saccharomyces cerevisiae*", by Hassid et al. *Journal of the American Chemical Society*, 63:295-298 (1941); "Comparative Tumor-Inhibitory and Anti-Bacterial Activity of Soluble and Particulate Glucan", by DiLuzio et al., *International Journal of Cancer*, 24:773-779 (1979).

SUMMARY OF THE INVENTION

By processing yeast cells and the glucans derived therefrom according to the techniques of the present invention, a glucan product which retains the three dimensional morphology of the intact yeast cell wall and having high water holding capacity is formed, which in turn may be further processed to give glucans having improved or novel functional properties.

In one embodiment of the present invention, there is provided a glucan derived from yeast which retains the intact cell wall structure of the yeast cell in vivo. Glucan particles having these properties is referred to as "whole glucan particles". A process for producing said glucan is also described. The process produces whole glucan which has a high level of purity, and consistency of the size and shape of the particle.

Whole glucan particles may be obtained from any glucan-containing source, including yeast or other fungi. The yeast is preferably a strain of *Saccharomyces cerevisiae*, but any strain of yeast can be used. These pure whole glucan particles are typically spherical, and exhibit a high water holding capacity, as exhibited by their viscosity in aqueous solutions. For example, an aqueous suspension of whole glucan particles derived from strain *Saccharomyces cerevisiae* A364A, having a particle size of approximately 2 to approximately 4 microns containing about 5.5 grams of glucan per deciliter has a viscosity of about 1000 centipoise. A *Saccharomyces cerevisiae* 374 derived glucan, having a particle size of from about 2.5 to about 6.3 microns, has a viscosity of about 2630 centipoise in an aqueous suspension containing about 3.5 grams of glucan per deciliter.

Further, in another embodiment of the present invention, there is provided aqueous hydroxide insoluble whole glucan particles derived from a mutant strain of yeast which has altered $\beta(1-6)$ linkages for enhancing the structural, biological and physical properties of the material. For example, the water holding capacity of whole glucan derived from these mutants by the present process is significantly enhanced. A method for producing the mutant yeast strains is provided.

Also provided is a glucan having altered $\beta(1-6)$ or altered $\beta(1-3)$ linkages for controlling the physical properties of the glucan particles, and methods for chemically altering the $\beta(1-6)$ and $\beta(1-3)$ linkages. The amount of $\beta(1-6)$ linked glucan can be decreased by treating the whole glucan with an acid (e.g., acetic acid). Decreasing the $\beta(1-6)$ linkages yields whole glucan particles with a higher water holding capacity, as evidenced by the greater aqueous viscosity of a suspension of the acid-modified whole glucan particles. Treating the whole glucan particles with a hydrolytic glucanase enzyme (e.g. laminarinase) decreases the amount of $\beta(1-3)$ linked glucan which yields whole glucan particles having a lower water holding capacity, as evidenced by the reduced aqueous viscosity of a suspension of the glucanase-modified whole glucan particles.

The term "altered" as used herein and applied to the structure of the glucan (i.e., the $\beta(1-6)$ or $\beta(1-3)$ linkages) shall be construed to mean that the glucan structure has been modified or changed in some way, endowing the altered glucan with properties which are measurably different from those of naturally occurring unmodified glucans.

The modified glucans set forth above can be produced by processes described hereinafter.

BRIEF DESCRIPTION OF THE FIGURES

FIG. 1 is a graph showing a plot of the viscosity profile of whole yeast glucan for *Saccharomyces cerevisiae* 374, 377 and A364A.

FIG. 2 is a graph showing a plot of the network-compression modulus vs. volume fraction for suspensions of whole glucan derived from *Saccharomyces cerevisiae* A364A and R4.

FIG. 3 is a graph showing a plot of the viscosity profile of whole glucan derived from *Saccharomyces cerevisiae* A364A after 4 hours of laminarinase digestion.

DETAILED DESCRIPTION OF THE INVENTION

The process described below for producing the glucan particles can be separated into two steps. The first step involves the extraction and purification of the alkali-insoluble whole glucan particles from the yeast or fungal cell walls. This process yields a product which maintains the morphological and structural properties of the glucan as found in vivo and will be referred to as a whole glucan, or whole glucan particles.

The second step, which is optional, involves the modification of the structure of the whole glucan particles by chemical or enzymatic treatment. In this step, the structure-function properties of the whole glucan particles obtained from the first step can be altered or modified in a controllable manner. For example, the the ratio of $\beta(1-6)/\beta(1-3)$ linkages can be chemically or enzymatically adjusted, thereby causing a commensurate change in the structural rigidity, hydrodynamic properties and biological properties of the whole glucan particles. The change in the hydrodynamic properties of the modified whole glucan particles can be evidenced by the change in the viscosity profile of an aqueous solution of the glucan particles. In this step, the amount of $\beta(1-6)$ linked glucan can be decreased by treating the whole glucan with acid (e.g., acetic acid) or with a $\beta(1-6)$ specific glucanase enzyme. The amount of $\beta(1-3)$ linked glucan can be decreased by treating the whole glucan particles with a $\beta(1-3)$ specific glucanase enzyme (e.g., laminarinase) or, alternatively, hydrolyzing with acids. Using these methods, the structure/function properties of the whole glucan particles can be controlled.

The structure-function properties of the whole glucan preparation depends directly on the source from which it is obtained. The source of whole glucan can be yeast or other fungi, or any other source containing glucan having the properties described herein. Yeast cells are a preferred source of glucans. The yeast strains employed in the present process can be any strain of yeast, including, for example, *Saccharomyces cerevisiae, Saccharomyces delbrueckii, Saccharomyces rosei, Saccharomyces microellipsodes, Saccharomyces carlsbergensis, Saccharomyces bisporus, Saccharomyces fermentati, Saccharomyces rouxii, Schizosaccharomyces pombe, Kluyveromyces polysporus, Candida albicans, Candida cloacae, Candida tropicalis, Candida utilis, Hansenula wingei, Hansenula arni, Hansenula henricii, Hansenula americana, Hansenula canadiensis, Hansenula capsulata, Hansenula polymorpha, Pichia kluyveri, Pichia pastoris, Pichia polymorpha, Pichia rhodanensis, Pichia ohmeri, Torulopsis bovina,* and *Torulopsis glabrata.* Mutants prepared from these or other yeast strains, can also be used, depending upon the biological and hydrodynamic properties desired. The yeast strain may be mutated, as will be described below, to affect the glucan structure and, hence, its properties. For example, mutations can be induced by which the relative amount of $\beta(1-6)$ or $\beta(1-3)$ linkages may be increased, or reduced, thereby causing a commensurate change in the structural rigidity, and the biological and hydrodynamic properties of the whole glucan particles. *Saccharomyces cerevisiae* and mutants therefrom are preferred strains. In particular, *Saccharomyces cerevisiae* A364A and its two temperature sensitive, cell division cycle mutants, *Saccharomyces cerevisiae* 374 and 377. The strain *Saccharomyces cerevisiae* R4 is a mutant of A364A which has been isolated on the basis of an increased $\beta(1-6)$ glucan fraction. The R4 mutant can also be employed to obtain glucan matrices with altered structure-function properties.

The following procedure was employed to prepare and isolate mutant R4, which has an increased number of $\beta(1-6)$ linkages, and can be used to prepare and isolate other yeast strains having altered $\beta(1-6)$ or $\beta(1-3)$ linkages:

Mutant strain R4 was derived from *Saccharomyces cerevisiae* A364A. The parent strain, A364A, was grown in YPD to mid-log phase. The cells were washed and divided into aliquots in sterile glass petri plates. The cells were exposed to a suitable mutagen, which in this case was UV exposure of 25 sec (30% survival). The cells were then suspended in YPD and grown under subdued light to a concentration of approximately $5 \times 10^6$ CFU/ml. The cells were harvested, and protoplasts were prepared by digesting the cells with 0.25 mg/ml of a glucanase enzyme, in this case laminarinase, for 30 minutes. Other hydrolytic enzymes which will degrade the cell wall can also be used. The suspension was then diluted with water to lyse osmotically sensitive protoplasts. The surviving cells then were grown in YPD to a density of approximately $5 \times 10^6$ CFU/ml (approximately 10 hours). Treatment with laminarinase, followed by growth was repeated two more times using 1.0 mg/ml enzyme for 15 minutes. The candidates which showed resistance to laminarinase digestion were then streaked on YPDA plates. Single colony isolates were tested for resistance to the enzyme compared to the resistance of the parent strain, A364A. The mutant R4 is available from the Agricultural Research Service under No. NRRL Y-15903.

The above procedure can be used to prepare and isolate other mutant yeast strains by using other parent strains as starting material. Other mutagens can be employed to induce the mutations, for example, chemical mutagens, irradiation, or other DNA and recombinant manipulations. Other selection or screening techniques may be similarly employed.

The yeast cells may be produced by methods known in the art. Typical growth media comprise, for example, glucose, peptone and a yeast extract. The yeast cells may be harvested and separated from the growth medium by methods typically applied to separate the biomass from the liquid medium. Such methods typically employ a solid-liquid separation process such as filtration or centrifugation. In the present process, the cells are preferably harvested in the mid-to late logarithmic phase of growth, to minimize the amount of glycogen and chitin in the yeast cells. Glycogen, chitin and protein are undesirable contaminants which affect the biological and hydrodynamic properties of the whole glucan particles.

The herein referred to first step according to the process of the present invention, involves treating the yeast with an aqueous alkaline solution at a suitable concentration to solubilize a portion of the yeast and form an alkali-hydroxide insoluble whole glucan particles having primarily $\beta(1-6)$ and $\beta(1-3)$ linkages. The alkali generally employed is an alkali-metal hydroxide, such as sodium or potassium hydroxide. Preferably, the starting material consists essentially of yeast separated from the growth medium. It is more difficult to control consumption of the aqueous hydroxide reactants and the concentration of reactants in the preferred ranges when starting with yeast compositions that are less concentrated. The yeast should have intact, unruptured cell walls since the preferred properties of the instant whole glucan particles depend upon an intact cell wall.

The treating step is performed by extracting the yeast in the aqueous hydroxide solution. The intracellular components and mannoprotein portion of the cell are solubilized in the aqueous hydroxide solution, leaving insoluble cell wall material which is substantially devoid of protein and having a substantially unaltered three dimensional matrix of $\beta(1-6)$ and $\beta(1-3)$ linked glucan. The preferred conditions of performing this step result in the mannan component of the cell wall being dissolved in the aqueous hydroxide solution. The intracellular constituents are hydrolyzed and released into the soluble phase. Preferably, the conditions of digestion are such that at least in a major portion of the cells, the three dimensional matrix structure of the cell walls is not destroyed. More preferably, substantially all the cell wall glucan remains unaltered and intact.

The aqueous hydroxide digestion step is preferably carried out in a hydroxide solution having initial normality of from about 0.1 to about 10.0. Typical hydroxide solutions include hydroxides of the alkali metal group and alkaline earth metals of the Periodic Table. The preferred aqueous hydroxide solutions are of sodium and potassium, due to their availability. The digestion is preferably carried out at a temperature of from about 20° C. to about 121° C. with lower temperatures requiring longer digestion times. When sodium hydroxide is used as the aqueous hydroxide, the temperature is preferably from about 80° C. to about 100° C. and the solution has an initial normality of from about 0.75 to about 1.5. The hydroxide added is in excess of the amount required, thus, no subsequent additions are necessary.

From about 10 to about 500 grams of dry yeast per liter of hydroxide solution is used. Preferably the aqueous hydroxide digestion step is carried out by a series of contacting steps so that the amount of residual contaminants such as proteins are less than if only one contacting step is utilized. In other words, it is desirable to remove substantially all of the protein material from the cell. Preferably such removal is carried out to such an extent that less than one percent of the protein remains with the insoluble cell wall glucan particles. An additional extraction step is preferably carried out in a mild acid solution having a pH of from about 2.0 to about 6.0. Typical mild acid solutions include hydrochloric acid, sodium chloride adjusted to the required pH with hydrochloric acid and acetate buffers. This extraction step is preferably carried out at a temperature of from about 20° C. to about 100° C. The digested glucan particles can be, if necessary, subjected to further washings and extraction to reduce the protein and contaminant level to the preferred amounts hereinbefore indicated.

By conducting this process without a step of disrupting the cell walls, the extraction can be conducted at more severe conditions of pH and temperature than was possible with the prior art procedure which included a step of disrupting the cell walls. That is, the process of this invention avoids product degradation while employing these severe extraction conditions which permits elimination of time-consuming multiple extraction steps.

After the above aqueous hydroxide treatment step, the final whole glucan product comprises about 10 to about 15 percent of the initial weight of the yeast cell, preferably the product is from about 12 to about 14 percent by weight.

The aqueous hydroxide insoluble whole glucan particles produced is as set forth in the summary of the invention. The whole glucan particles can be further processed and/or further purified, as desired. For example, the glucan can be dried to a fine powder (e.g., by drying in an oven); or can be treated with organic solvents (e.g., alcohols, ether, acetone, methyl ethyl ketone, chloroform) to remove any traces or organic-soluble material, or retreated with hydroxide solution, to remove additional proteins or other impurities which may be present.

The whole glucan particles obtained from the present process are comprised of highly pure glucan, which consists essentially of $\beta(1-6)$ and $\beta(1-3)$ linked glucan. The whole glucan particles contain very little contamination from protein and glycogen. Preferably, the whole glucan particles are spherical in shape with a diameter of about 2 to about 10 microns and contain greater than 85% by weight hexose sugars, approximately 1% by weight protein and no detectable amount of mannan, as determined by Fourier Transform Infrared Spectroscopy. Glucans obtained by prior processes contain substantially higher quantities of chitin and glycogen than the present glucans.

The second step as set forth above, involves the modification of the whole glucan particles, as produced above, by chemical treatment to change the properties of the glucan. It is contemplated that whole glucan particles, derived from any yeast strain may be used, in addition to those particular strains described herein. As mentioned above, a very broad spectrum of yeast strains may be used. The processing conditions described above are also applicable to glucan extraction from fungi in general. The properties of these glucans also will depend on the sources from which they are derived.

According to a first chemical treatment, the whole glucan particles can be treated with an acid to decrease the amount of $\beta(1-6)$ linkages and thus, change the hydrodynamic properties of said glucans as evidenced by an increase in the viscosity of aqueous solutions of these modified glucans.

In accordance with the principles of the present invention, there is provided a process for preparing an altered whole glucan particles by treating the glucan particles with an acid, for a suitable period of time to alter the $\beta(1-6)$ linkages. Acetic acid is preferred, due to its mild acidity, ease of handling, low toxicity, low cost and availability, but other acids may be used. Generally these acids should be mild enough to limit hydrolysis of the $\beta(1-3)$ linkages. The treatment is carried out under conditions to substantially only affect the $\beta(1-6)$ linked glucans. Preferably, the acid treatment is carried out with a liquid consisting essentially of acetic acid, or any dilutions thereof (typical diluents can be organic solvents or inorganic acid solutions). The treatment is preferably carried out at a temperature of from about 20° C. to about 100° C. Preferably, the treatment is carried out to such an extent to remove from about 3 to about 20 percent by weight of acid soluble material based on total weight of the whole glucan particles before treatment. More preferably, the extent of removal is from about 3 to about 4 percent by weight. The preferred compositions formed demonstrate altered hydrodynamic properties and an enhancement in viscosity after treatment.

According to a second chemical treatment, the whole glucan particles are treated with an enzyme or an acid, to change the amount of $\beta(1-3)$ linkages. For whole glucan particles derived from some yeast strains, enzyme treatment causes a decrease in the viscosity, and for others, it causes an increase in viscosity, but in general, alters the chemical and hydrodynamic properties of the resulting glucans. The treatment is with a $\beta(1-3)$ glucanase enzyme, such as laminarinase, for altering the $\beta(1-3)$ linkages to alter the hydrodynamic properties of the whole glucan particles in aqueous suspensions.

The enzyme treatment can be carried out in an aqueous solution having a concentration of glucan of from about 0.1 to about 10.0 grams per liter. Any hydrolytic glucanase enzyme can be used, such as laminarinase, which is effective and readily available. The time of incubation may vary depending on the concentration of whole glucan particles and glucanase enzyme. The $\beta(1-3)$ linkages are resistant to hydrolysis by mild acids such as acetic acid. Treatment with strong or concentrated acids, such as hydrochloric acid (HCl), sulfuric acid ($H_2SO_4$) or formic acid, hydrolyzes the $\beta(1-3)$ linkages thereby reducing the amount of $\beta(1-3)$ linkages. The acid treatment can be carried out in an aqueous solution having a concentration of glucan from about 0.1 to about 10.0 grams per liter. The time of acid treatment may vary depending upon the concentration of whole glucan particles and acid. Acid hydrolysis can be carried out at a temperature of from about 20° C. to about 100° C. The preferred compositions formed demonstrate altered hydrodynamic properties.

By controlling the incubation time, it is possible to control the chemical and hydrodynamic properties of the resulting product. For example, the product viscosity can be precisely controlled for particular usage, as, for example, with a variety of food products.

A hydrodynamic parameter ($K_1$) of the final treated product having altered linkages is dependent on the treatment time according to the final formula:

$$K_1 = -0.0021 \text{ (time)} + 0.26$$

where time is in minutes
where time is less than one hour.

The parameter $K_1$ is directly related (proportional) to the relative viscosity. In the case of aqueous suspensions the relative viscosity is equal to the actual viscosity when the latter is measured in centipoise.

A process for preparing an aqueous slurry of a glucan having a predetermined desired viscosity is provided. The slurry comprises glucan at a concentration which is a function of the predetermined desired viscosity according to the following approximate formula:

$$\frac{1}{\text{concentration}} = K_1 \frac{1}{\log(\text{relative viscosity})} + K_2$$

where,
$K_1$ = (shape factor) × (hydrodynamic volume)
$K_2$ = (hydrodynamic volume)/(maximum packing fraction)

The shape factor is an empirically determined value which describes the shape of the glucan matrix in its aqueous environment. The shape factor is a function of the length:width ratio of a particle and can be determined microscopically. The hydrodynamic volume is a measure of the volume a particle occupies when in suspension. This is an important parameter for glucan suspensions at it indicates the high water holding capacity of glucan matrices. The maximum packing fraction can be described as the highest attainable volume fraction of glucans which can be packed into a unit volume of suspension.

The invention is further illustrated by the following examples.

EXAMPLE 1

In this example, whole glucan is prepared from *Saccharomyces cerevisiae* A364A, 374, 377 and R4. A 14 liter Chemap fermenter was used to produce the biomass in 10 liters of growth medium which comprised 2% glucose, 2% peptone and 1% yeast extract. The fermenter was inoculated with 250 ml of a stationary phase culture and operated at a temperature of about 28°–30° C., 400 rpm impeller speed, 1 vvm aeration rate and a pH of 5.5±0.1. The growth of the cells was followed by removing 10 milliliter samples and measuring the turbidity in a Klett-Summerson colorimeter. In the fermentation of strains 374 and 377 a temperature shift to 37° C. was performed at the early exponential growth phase. This was equivalent to a Klett reading of approximately 30 units.

The fermentation was stopped at the late exponential growth phase, which corresponds to approximately 120 Klett units.

The cells were harvested by batch centrifugation at 8000 rpm for 20 minutes in a Sorval RC2-B centrifuge. The cells were then washed twice in distilled water in order to prepare them for the extraction of the whole glucan. The first step involved resuspending the cell mass in 1 liter 4% w/v NaOH and heating to 100° C. The cell suspension was stirred vigorously for 1 hour at this temperature. The insoluble material containing the cell walls was recovered by centrifuging at 2000 rpm for 15 minutes. This material was then suspended in 2 liters, 3% w/v NaOH and heated to 75° C. The suspension was stirred vigorously for 3 hours at this temperature. The suspension was then allowed to cool to room temperature and the extraction was continued for a further 16 hours. The insoluble residue was recovered by centrifugation at 2000 rpm for 15 minutes. This material was finally extracted in 2 liters, 3% w/v NaOH brought to pH 4.5 with HCl, at 75° C. for 1 hour. The insoluble residue was recovered by centrifugation and washed three times with 200 milliliters water, once with 200 milliliters dehydrated ethanol and twice with 200 milliliters dehydrated ethyl ether. The resulting slurry was placed on petri plates and air dried at 37° C. for 12 hours to a fine white powder. An example of the yields obtained from this extraction and purification process is shown in Table 1:

TABLE 1

Yields of Whole Glucan Particles from Saccharomyces cerevisiae A364A

| Batch # | 1 | 2 | 3 |
|---|---|---|---|
| Dry cell weight, DCW, (g) | 14.03 | 15.25 | 9.78 |
| Whole Glucan Particles (g) | 1.86 | 1.64 | 1.53 |
| % DCW extracted | 13 | 11 | 15 |
| Protein content[1] (% w/w) | 0.73 | 0.81 | 0.88 |

Although a small quantity of protein was detected in the whole glucan particles, it was proven that the overwhelming component in this preparation was $\beta$-glucan. The purity of this preparation was tested by obtaining infra-red spectra of the whole glucan samples. Samples were prepared in solid KBr discs and analyzed in a Perkin-Elmer infra-red Spectrophotometer. The spectra obtained were compared with the spectrum of a standard $\beta$-glucan, Laminarin, purchased from Sigma Chemical Company. The whole glucan samples from all three strains gave characteristic spectra of glucan. All the peaks characteristic of the $\beta$-glucan structural backbone at 7.95, 8.35, 8.7 and 11.3 m were obtained for all the whole glucan samples.

The whole glucan particles were then rehydrated in distilled water in order to determine the viscosity profile of the suspension. Viscosity was measured using a Cannon-Fenske capillary viscometer (size 75). The viscosity profiles of whole glucan particle suspensions for the three strains are shown in FIG. 1.

The units of concentration in g/dl (g/100 milliliters) are equivalent to % w/v. By applying the linear model which was discussed in the detailed description of this disclosure, the relevant information concerning the hydrodynamic properties of the whole glucan particles was obtained. The accuracy of this model is reflected in the values of the regression coefficient, r, shown in Table 2:

TABLE 2

Hydrodynamic Properties of Whole Glucan Particles

| Glucan Sample | Regression Coefficient r | Shape Factor v | Hydrodynamic Volume v (dl/g) | $\Phi_m$ |
|---|---|---|---|---|
| A364A | 0.9986 | 2.5 | 0.092 | 0.63 |
| 374 | 0.9987 | 4.1 | 0.088 | 0.36 |
| 377 | 0.9974 | 4.1 | 0.091 | 0.45 |
| R4 | 0.9995 | 2.5 | 0.087 | .66 |

1. $\Phi_m$ = Maximum packing fraction

The whole glucan particles produced from mutant R4 has a similar viscosity profile to that of whole glucan from A364A, however, by increasing the degree of $\beta(1-6)$ crosslinking in vivo a glucan matrix has been developed with a significantly higher mechanical strength as shown in Table 5. The strength (rigidity) of the glucan matrices was measured using centrifugal compression of the glucan matrices.

Table 3 illustrates the structural rigidity (elastic modulus) of whole glucan matrices.

TABLE 3

The Elastic Modulus of Whole Glucan Matrices Measured in the Range 0–30 g

| Source | Network Modulus (Nm$^{-2}$) | | | |
|---|---|---|---|---|
| | $\Phi = 0.048$ | 0.050 | 0.052 | 0.054 |
| A363A Whole Glucan | 170 | 225 | 310 | 480 |

TABLE 3-continued

The Elastic Modulus of Whole Glucan Matrices Measured in the Range 0–30 g

| Source | Network Modulus (Nm$^{-2}$) | | | |
|---|---|---|---|---|
| | $\Phi = 0.048$ | 0.050 | 0.052 | 0.054 |
| R4 Whole Glucan | 1300 | 2400 | 6000 | 42000 |

Comparison With Glucan Prepared By Prior Art Method

Whole glucan produced by the above method was compared to glucan prepared by a prior art method.

Glucan material was prepared according to the procedure described in Manners, et al., in *Biochem. J.*, 135:31-36 (1973). This material was then used in a number of assays performed in parallel with glucans prepared by Applicants procedure from strains A364A and R4. The following data was obtained:
1. Protein content
2. Presence and level of glycogen
3. Relative levels of chitin The functional component of the yeast cell wall in terms of solution properties and water-holding capacity is solely the beta-glucan. It is therefore important to minimize the levels of the above contaminants for two reasons: first, that the presence of hydrophobic contaminants such as proteins and glycogen will hinder the functional properties of the glucan matrix; secondly, the purity of the preparation is an essential factor when considerating the application of glucans in both the pharmaceutical and food industries.

Protein content was determined chemically using the Bio-Rad assay (Bio-Rad). In this procedure, glucan samples were suspended in water to a concentration of 5 mg/ml, and lysozyme solutions in the range of 0.2 to 1.0 mg/ml were prepared as standards. Duplicate 1.0 ml aliquots of the samples and standards were placed in clean dry test tubes and 5.0 ml of the undiluted dye reagent was added. The solutions were vortexed, and after 5 minutes, the optical density (O.D.) was measured at 595 nm. A water blank was used as a negative control.

Total hexose was measured in duplicate 100-fold dilutions of glucan suspensions. A standard curve was prepared using glucose solutions in the range of 10-100 ug/ml. Duplicate 1.0 ml aliquots of the samples were placed in clean dry test tubes, and 1.0 ml of 5% (v/v) phenol was added. Then, 5 ml of concentrated sulfuric acid ($H_2SO_4$) was added to each tube, the mixture was vortexed, and incubated at 37° C. for 15-20 minutes. The optical density was measured at 488 nm with a water sample as the blank. The results are shown in Table 4.

TABLE 4

Protein Contamination of Glucan Particles

| Preparation | Protein mg/ml | Hexose mg/ml | Protein/Hexose |
|---|---|---|---|
| A364A | 0.071 | 8.74 | 0.0081 |
| R4 | 0.082 | 8.81 | 0.0093 |
| Manner's Prep | 1.808 | 8.88 | 0.2036 |

Manner's preparation contained protein levels approximately 25 times higher than those of glucans prepared by the present procedure.

Fourier-Transform Infrared (FT-IR) spectroscopy was used to detect the presence of chitin and glycogen, and peak integration was used to determine their relative levels. The characteristic glycogen peaks which appear at a wave number of 850, 930 and 760 cm$^{-1}$ were not detected in the preparations made according to Applicants' procedure, but were clearly present in Manners' preparation. In addition, the characteristic chitin absorbance at 1550 cm$^{-1}$ was significantly stronger for the Manner's preparation. These results were quantitated and are summarized in Table 5.

TABLE 5

Contaminating Polysaccharides In Glucan Preparations

| Contaminant | Preparation Whole Glucan Particles (strain A364A) | Manner's Glucan |
|---|---|---|
| Glycogen | 1 | 9.4 |
| Chitin | 1 | 2.9 |

Manner's preparation contains approximately 10-fold higher glycogen and 3-fold higher chitin levels.

The higher protein content in Manner's preparation is a direct result of the extraction procedure used. Manners' process does not result in adequate hydrolysis and removal of the protein. The increased glycogen and chitin is due to two factors. The primary factor is the age of the yeast cells found in commercial baker's yeast, which is in the stationary growth phase. In the present process the growth rate of the yeast cell is closely monitored, and harvested in the late-logarithmic phase, and before the cells enter the stationary phase. The second factor the extraction procedure. Table 6 illustrates the significant compositional differences resulting from Manners' procedure and the Applicants' procedure:

TABLE 6

Composition of Glucans

| Component | Whole Glucan Particles (A364A) mg | % | Manner's Glucan mg | % |
|---|---|---|---|---|
| Glucan | 1000 | 96.2 | 1000 | 51.8 |
| Protein | 8 | 0.8 | 351 | 18.2 |
| Glycogen | 31 | 2.9 | 579 | 30.0 |

On a basis of 1000 mg pure glucan, the whole glucan material produced by the process of the invention contains only 39 mg of contaminants as compared to 930 mg for the Manners' preparation. This contaminant mass displaces its weight in water from the glucan particles resulting in a considerably lower water holding capacity.

The present process results in a glucan product substantially different than that obtained from the procedure described by Manners, et al. The Manners product has much higher levels of protein and glycogen contamination, which results in a glucan product which lacks the water holding properties of the Applicants' product. In addition, the results clearly indicate that Manners' procedure produces in an impure glucan product, which is only about fifty-two (52%) percent glucan. The present procedure yields a glucan product of about ninety-six (96%) percent purity (see Table 6 above).

EXAMPLE 2

This example concerns the acid treatment of Saccharomyces cerevisiae A364A whole glucan using acetic acid. A 500 mg sample of whole glucan from S. cerevisiae A364A produced by the method of Example 1 was suspended in 250 milliliters of 0.5M acetic acid. The suspension was continuously stirred at 90° C. for 3 hours. At the end of this extraction, the remaining insoluble glucan residue was recovered by batch centrifugation at 5000 rpm for 20 minutes. The glucan residue was washed once in 200 milliliters distilled water, once in 200 milliliters dehydrated ethanol and twice in 200 milliliters dehydrated ethyl ether. The resulting slurry was dried in air at 37° C. for 12 hours. The initial suspension in acetic acid and the supernatant were assayed for total carbohydrate to determine the proportion of the extractable β(1-6) glucan component. The white glucan powder obtained after drying was resuspended in distilled water to determine its viscosity profile. Chemical modification of A364A glucan by acetic acid had an insignificant effect on the viscosity characteristics. However, measurement of the elastic modulus of the glucan matrices showed that their structural rigidity can be controlled by the extent of the acetic acid extraction. FIG. 2 illustrates the effect of the acetic extraction on the structural rigidity of whole glucan derived from strain A364A and compares this to glucan extracted from strain R4.

EXAMPLE 3

A 500 milligram sample of whole glucan from Saccharomyces cerevisiae 374 produced by the method of Example 1 was suspended in 250 milliliters, 0.5M acetic acid. An identical procedure to that outlined in Example 2 was followed. In this case, extraction in hot acetic acid caused an increase in the thickening properties of the glucan as shown in Table 7.

TABLE 7

The Viscosity of a Suspension of 374 Whole Glucan Compared to 374 Glucan After Acetic Acid Extraction for a Range of Concentrations

| | Viscosity in Centipoise, 25° C. | | | |
|---|---|---|---|---|
| Source of Glucan | 2% | 2.5% | 3% | 3.5% |
| 374 (Whole Glucan) | 1.5 | 2.8 | 7.1 | 14.2 |
| 374 (After Extraction) | 1.6 | 4.7 | 58.3 | 1879.0 |

EXAMPLE 4

A 500 milligram sample of 377 whole glucan produced by the method of Example 1, was suspended in 150 milliliters, 0.5M acetic acid. An identical procedure to that outlined in Example 2 was followed.

The effect of this process on the viscosity profile of 377 glucan is shown in Table 8.

TABLE 8

The Viscosity of a Suspension of 377 Whole Glucan Compared to 377 Glucan After Acetic Acid Extraction for a Range of Concentration

| | Viscosity in Centipoise, 25° C. | | | |
|---|---|---|---|---|
| Source of Glucan | 2% | 2.5% | 3% | 3.5% |
| 377 (Whole Glucan) | 1.6 | 3.4 | 16.0 | 75.0 |
| 377 (After Extraction) | 1.7 | 4.7 | 58.3 | 1878.0 |

EXAMPLE 5

A 500 milligram sample of whole glucan from Saccharomyces cerevisiae R4 produced by the method of Example 1 was suspended in 250 milliliters, 0.5M acetic acid. An identical procedure to that outlined in Example 2 was followed.

In this case the whole glucan sample before modification, has an identical viscosity profile to the whole glucan from strain A364A; however, after the extraction the thickening properties are enhanced considerably, as shown in Table 9.

TABLE 9

The Viscosity of a Suspension of R4 Whole Glucan Compared to R4 Glucan After Acid Extraction for a Range of Concentrations

| Source of Glucan | Viscosity in Centipoise, 25° C. | | | | |
|---|---|---|---|---|---|
| | 2% | 2.5% | 3% | 3.5% | 3.7% |
| R4 (Whole Glucan) | 1.8 | 2.3 | 3.1 | 4.5 | 5.4 |
| R4 (After Extraction) | 2.6 | 4.6 | 12.4 | 106.3 | 636.7 |

The effect of the acetic acid treatment on the hydrodynamic properties of the glucan extracted from strains A364A, 374, 377 and R4, as determined by the linear model, is summarized in Table 10.

TABLE 10

Hydrodynamic Properties of Glucan After Acetic Acid Extraction

| Sample | Regression Coefficient r | Shape Factor v | Hydrodynamic Volume v (dl/g) | $\Phi_m$ |
|---|---|---|---|---|
| A364A Whole Glucan | 0.9999 | 2.5 | 0.106 | 0.46 |
| A364A After Extn. | 0.9974 | 2.5 | 0.103 | 0.47 |
| 374 Whole Glucan | 0.9981 | 4.1 | 0.088 | 0.60 |
| 374 After Extn. | 0.9995 | 4.1 | 0.103 | 0.44 |
| 377 Whole Glucan | 0.9997 | 4.1 | 0.091 | 0.45 |
| 377 After Extn. | 0.9995 | 4.1 | 0.103 | 0.44 |
| R4 Whole Glucan | 0.9995 | 2.5 | 0.087 | 0.66 |
| R4 After Extn. | 0.9988 | 2.5 | 0.103 | 0.44 |

$\Phi_m$ = Maximum packing fraction

EXAMPLE 6

Treatment of whole glucan from *Saccharomyces cerevisiae* A364A with Laminarinase A 400 milliliter solution containing 1 milligram/milliliter whole glucan produced by the method of Example 1, and 0.25 milligram/milliliter Laminarinase (endo $\beta(1-3)$ glucanase) was prepared in phosphate buffer at pH 7.0. The solution was incubated at 37° C. for 4 hours. At the end of the incubation the solution was held at 70° C. for 15 minutes to deactivate the enzyme. The remaining residue was recovered by centrifugation at 5000 rpm for 20 minutes. The resulting glucan residue was diluted into range of concentrations in order to obtain viscosity measurements of the Laminarinase-degraded glucan sample. Since the enzyme cannot be effectively removed from solution, a control experiment was performed as above where the incubated enzyme contained no glucan. These readings were then used to correct the solvent viscosity accounting for the contribution of the enzyme to the macroscopic viscosity of the suspension. The effect of this process on the viscosity profile of an A364A glucan suspension is shown in FIG. 3, and in Table 11.

Table 11 shows the pronounced effect of the enzyme treatment on the glucan. At a concentration of 3.7% w/v an 80-fold decrease in the viscosity has been achieved.

TABLE 11

The Viscosity of Suspension of A364A Glucan Before and After the Enzyme Modification for a Range of Concentrations

| Source of Glucan | Viscosity in Centipoise 25° C. | | | | |
|---|---|---|---|---|---|
| | 1% | 2% | 3% | 3.5% | 3.7% |
| A364A (Whole Glucan) | 1.4 | 2.7 | 13.7 | 127.3 | 816.3 |
| A364A (After Enzymatic Digestion) | 1.2 | 1.6 | 3.1 | 6.4 | 10.2 |

EXAMPLE 7

Treatment of Whole Glucan From *Saccharomyces cerevisiae* 374 with Laminarinase

A sample of 374 whole glucan was subjected to the process outlined in detail in Example 6. This process caused a decrease in the thickening properties of this glucan preparation as shown in Table 12.

TABLE 12

The Viscosity of Suspension of 374 Glucan Before and After the Enzyme Modification for a Range of Concentrations

| Source of Glucan | Viscocity in Centipoise. 25° C. | | | |
|---|---|---|---|---|
| | 1% | 2% | 3% | 3.5% |
| 374 (Whole Glucan) | 1.6 | 4.0 | 47.4 | 2630.7 |
| 374 (After Enzymatic Digestion) | 1.3 | 2.3 | 9.3 | 62.9 |

EXAMPLE 8

Treatment of whole glucan from *Saccharomyces cerevisiae* 377 with Laminarinase

A sample of 377 whole glucan was subjected to the process outlined in detail in Example 5. The effect of this process on this glucan preparation was similar to that on 374 glucan up to a concentration of 2% w/v. However, at higher concentrations the viscosity of the treated glucan was higher. This product therefore possesses extremely valuable properties since it has a negligible effect on suspension viscosities of low concentrations yet exhibits very high thickening properties at concentrations above 3% w/v. Table 13 below quantitatively describes the thickening properties of this product.

TABLE 13

The Viscosity of Suspension of 377 Glucan Before and After the Enzyme Modification for a Range of Concentrations

| Source of Glucan | Viscocity in Centipoise. 25° C. | | | |
|---|---|---|---|---|
| | 1% | 2% | 3% | 3.5% |
| 377 (Whole Glucan) | 1.6 | 3.4 | 16.0 | 75.0 |
| 377 (After Enzymatic Digestion | 1.4 | 2.8 | 18.1 | 367.4 |

The effect of this enzyme digest on the hydrodynamic properties of the glucan samples from strains A364A, 374, and 377 is summarized in Table 14.

TABLE 14

| Sample | Hydrodynamic Properties of Glucan After Laminarinase Digest | | | |
|---|---|---|---|---|
| | Regression Coefficient r | Shape Factor V | Hydrodynamic Volume v (dl/g) | $\Phi_m$ |
| A364A Whole Glucan | 0.999 | 2.5 | 0.106 | 0.46 |
| A364A After Digest | 0.9998 | 2.5 | 0.057 | 0.27 |
| 374 Whole Glucan | 0.9987 | 4.1 | 0.088 | 0.36 |
| 374 After Digest | 0.9985 | 4.1 | 0.070 | 0.30 |
| 377 Whole Glucan | 0.9974 | 4.1 | 0.091 | 0.45 |
| 377 After Digest | 0.9989 | 4.1 | 0.065 | 0.27 |

$\Phi_m$ = Maximum packing fraction

Equivalents

Those skilled in the art will recognize, or be able to ascertain using no more than routine experimentation, many equivalents to the specific embodiments of the invention described herein. Such equivalents are intended to be encompassed by the following claims.

We claim:

1. Whole glucan particles isolated from glucan-containing cell walls and substantially retaining the in vivo glucan morphology.

2. Whole glucan particles of claim 1 isolated from yeast cells.

3. Whole glucan particles of claim 2 wherein said yeast cells comprise a strain selected from the group consisting of:

Saccharomyces cerevisiae, Saccharomyces delbrueckii, Saccharomyces rosei, Saccaromyces microellipsodes, Saccharomyces carlsbergensis, Saccharomyces bisporus, Saccharomyces fermentati, Saccharomyces rouxii, Schizosaccharomyces pombe, Kluyveromyces lactis, Kluyveromyces fragilis, Kluyveromyces polysporus, Candida albicans, Candida cloacae, Candida-tropicalis, Candida utilis, Hansenula wingei, Hansenula arni, Hansenula henricii, Hansenula americana, Hansenula canadiensis, Hansenula capsulata, Hansenula polymorpha, Pichia kluyveri, Pichia pastoris, Pichia polymorpha, Pichia rhodanensis, Pichia ohmeri, Torulopsis bovina and Torulopsis glabrata.

4. Whole glucan particles of claim 2 wherein the yeast cells are a strain of Saccharomyces cerevisiae yeast.

5. Whole glucan particles of claim 4 consisting essentially of glucans having $\beta(1-6)$ and $\beta(1-3)$ linkages.

6. Whole glucan particles of claim 5 containing less than about one percent, by weight, protein.

7. Whole glucan particles of claim 6 having a spherical shape with an average particle size of from about 2 to about 10 microns.

8. Whole glucan particles derived from yeast cells and having substantially the in vivo glucan morphology, said glucan particles containing less than about one percent, by weight, protein and being spherical in shape with an average particle size of from about 2 to about 10 microns.

9. Whole glucan particles derived from yeast cells, said particles being alkali-insoluble and having substantially the in vivo glucan morphology, said particles also having a spherical morphology with an average particle diameter of from about 2 to about 10 microns and containing greater than 85%, by weight, hexose sugars and less than about one percent, by weight, protein.

10. A process for preparing whole glucan particles having substantially the in vivo glucan morphology, comprising extracting alkali-soluble components from glucan-containing cells walls without a prior disruption step for said cell walls to thereby produce whole glucan particles retaining the in vivo glucan morphology.

11. A process of claim 10 wherein said glucan-containing cell walls comprise yeast cell walls.

12. A process of claim 11 wherein the yeast cell walls originate from cells comprising a strain selected from the group consisting of:

Saccharomyces cerevisiae, Saccharomyces delbrueckii, Saccharomyces rosei, Saccaromyces microellipsodes, Saccharomyces carlsbergensis, Saccharomyces bisporus, Saccharomyces fermentati, Saccharomyces rouxii, Schizosaccharomyces pombe, Kluyveromyces lactis, Kluyveromyces fragilis, Kluyveromyces polysporus, Candida albicans, Candida cloacae, Candida-tropicalis, Candida utilis, Hansenula wingei, Hansenula arni, Hansenula henricii, Hansenula americana, Hansenula canadiensis, Hansenula capsulata, Hansenula polymorpha, Pichia kluyveri, Pichia pastoris, Pichia polymorpha, Pichia rhodanensis, Pichia ohmeri, Torulopsis bovina and Torulopsis glabrata.

13. A process of claim 12 wherein said extraction step is performed by contacting the yeast cells with an aqueous basic solution.

14. A process of claim 13 wherein said aqueous basic solution has a normality of from about 0.1 to about 10.

15. A process of claim 14 wherein said aqueous basic solution comprises a hydroxide solution.

16. A process of claim 15 wherein said hydroxide solution comprises a sodium hydroxide solution.

17. A process of claim 16 wherein the concentration of yeast cell mass in the aqueous hydroxide solution is from about 10 to about 500 grams of dry cell weight per liter of aqueous hydroxide solution.

18. A process of claim 17 wherein the temperature during the extraction step is maintained from about 20° C. to about 121° C.

19. A process according to claim 10 wherein the extraction step is performed by contacting the glucan-containing cell walls with an aqueous hydroxide solution having a pH of from about 2 to about 6 and a temperature of from about 20° C. to about 121° C.

20. A process of claim 19 including the additional step of subsequently drying the glucan particles obtained to produce a fine powder.

21. A process of claim 20 wherein the whole glucan particles are contacted with an organic solvent to further purify said particles prior to drying them to a fine powder.

22. A process of claim 21 wherein the purified and dried glucan particles are re-treated with an aqueous hydroxide solution to remove additional soluble protein portions.

23. Whole glucan particles produced by the method of claim 10.

24. Whole glucan particles produced by the method of claim 19.

25. Whole glucan particles produced by the method of claim 22.

* * * * *